United States Patent
Mori et al.

(10) Patent No.: US 8,420,995 B2
(45) Date of Patent: Apr. 16, 2013

(54) SOLID-STATE IMAGING DEVICE

(75) Inventors: Harumichi Mori, Hamamatsu (JP);
Ryuji Kyushima, Hamamatsu (JP);
Kazuki Fujita, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 55 days.

(21) Appl. No.: 13/202,995

(22) PCT Filed: Mar. 26, 2010

(86) PCT No.: PCT/JP2010/055418
§ 371 (c)(1),
(2), (4) Date: Aug. 24, 2011

(87) PCT Pub. No.: WO2010/113810
PCT Pub. Date: Oct. 7, 2010

(65) Prior Publication Data
US 2011/0303823 A1    Dec. 15, 2011

(30) Foreign Application Priority Data
Apr. 1, 2009  (JP) ................................. 2009-089247

(51) Int. Cl.
*H01L 27/146* (2006.01)
(52) U.S. Cl.
USPC ..................................... 250/208.1; 348/230.1
(58) Field of Classification Search ............... 250/208.1; 348/230.1, 302, 304
See application file for complete search history.

(56) References Cited

U.S. PATENT DOCUMENTS

| | | | |
|---|---|---|---|
| 6,972,791 B1 * | 12/2005 | Yomeyama | 348/230.1 |
| 7,460,165 B2 | 12/2008 | Anderson et al. | |
| 7,462,807 B2 | 12/2008 | Caupain et al. | |
| 7,711,085 B2 | 5/2010 | Suzuki et al. | |
| 7,816,752 B2 * | 10/2010 | Mori | 257/446 |
| 8,237,808 B2 * | 8/2012 | Matsumoto et al. | 348/222.1 |
| 2005/0151864 A1 | 7/2005 | Anderson et al. | |
| 2006/0237625 A1 | 10/2006 | Caupain et al. | |
| 2006/0273359 A1 * | 12/2006 | Mori | 257/291 |
| 2008/0170137 A1 * | 7/2008 | Matsumoto et al. | 348/241 |
| 2009/0041191 A1 | 2/2009 | Suzuki et al. | |

FOREIGN PATENT DOCUMENTS

| | | |
|---|---|---|
| CA | 2 528 811 | 1/2005 |
| DE | 11 2006 000 869 | 2/2008 |
| EP | 1 671 371 | 8/2008 |
| FR | 2 857 160 | 1/2005 |
| GB | 2 409 944 | 7/2005 |

(Continued)

*Primary Examiner* — Seung C Sohn
(74) *Attorney, Agent, or Firm* — Drinker Biddle & Reath LLP

(57) ABSTRACT

A solid-state imaging device of one embodiment includes a light receiving section including of a plurality of pixels 11 having respective photodiodes, the pixels being two-dimensionally arrayed in M rows and N columns; N readout lines disposed for the respective columns and connected with the photodiodes PD included in the pixels of a respective columns via readout switches; a signal output section for outputting a voltage value according to an amount of charge input through each of the readout lines; and a vertical shift register for controlling an opening and closing operation of the readout switch for each of the rows. A contour between one side along a row direction of the light receiving section and a pair of sides along a column direction has a stepped shape. A dummy photodiode region is formed along the stepped contour of the light receiving section.

7 Claims, 8 Drawing Sheets

FOREIGN PATENT DOCUMENTS

| | | |
|---|---|---|
| JP | 2002-232291 | 8/2002 |
| JP | 3507800 | 12/2003 |
| JP | 2005-197747 | 7/2005 |
| JP | 2006-314774 | 11/2006 |
| JP | 2007-144137 | 6/2007 |
| JP | 2008-228866 | 10/2008 |
| JP | 2009-513166 | 4/2009 |
| JP | 2009-131656 | 6/2009 |
| JP | 4503573 | 4/2010 |
| JP | 4536062 | 6/2010 |
| WO | 2005/004239 | 1/2005 |
| WO | 2006/109808 | 10/2006 |

* cited by examiner (a)

(b)

ical Field
SOLID-STATE IMAGING DEVICE

TECHNICAL FIELD

The present invention relates to a solid-state imaging device.

BACKGROUND ART

As solid-state imaging devices, solid-state imaging devices using CMOS technology are known, and among these, a passive pixel sensor (PPS) type solid-state imaging device is known. The PPS type solid-state imaging device includes a light receiving section in which PPS type pixels including photodiodes each for generating charge of an amount according to an incident light intensity are two-dimensionally arrayed in M rows and N columns, and, in each pixel, accumulates charge generated in the photodiode in response to light incidence in a capacitive element of an integration circuit, and outputs a voltage value according to the accumulated charge amount.

Generally, an output terminal of each of the M pixels of each column is connected with an input terminal of an integration circuit provided corresponding to the column via a readout line provided corresponding to the column. And, in sequence from the first row to the M-th row and row by row, charges generated in the photodiodes of the pixels are input to a corresponding integration circuit through a corresponding readout line, and a voltage value according to the charge amount is output from the integration circuit.

The PPS type solid-state imaging device is used for various purposes. For example, such a solid-state imaging device is used in combination with a scintillator section as an X-ray flat panel also for medical purposes and industrial purposes, and further specifically used also in an X-ray CT apparatus, a microfocus X-ray inspection system, etc. An X-ray inspection system disclosed in Patent Literature 1 is a system that images X-rays output from an X-ray generator and transmitted through an inspection object by a solid-state imaging device to inspect the inspection object, and is capable of imaging X-rays transmitted through the inspection object by the solid-state imaging device in a plurality of types of imaging modes. These multiple types of imaging modes are mutually different in an imaging region in the light receiving section.

CITATION LIST

Patent Literature

Patent Literature 1: Pamphlet of International Publication No. WO2006/109808

SUMMARY OF INVENTION

Technical Problem

Conventionally, the size of the light receiving section of the solid-state imaging device described above has been limited by the size of a semiconductor wafer to serve as material. That is, when a rectangular solid-state imaging device is produced from a substantially circular semiconductor wafer, the maximum shape of the solid-state imaging device is a rectangle that inscribes the semiconductor wafer. However, depending on the purpose of the solid-state imaging device, a light receiving section of a larger area is desired in some cases. In a dental X-ray imaging system, for example, the shape of an imaging region required for the solid-state imaging device varies depending on a variety of imaging modes such as a panoramic mode and a CT mode, and in order to realize these imaging modes by the single solid-state imaging device, it has been required to house the respective imaging regions in these imaging modes in a single light receiving section.

It is an object of the present invention to provide a solid-state imaging device capable of obtaining a light receiving section of a larger area under limitations due to the size of a semiconductor wafer to serve as material.

Solution to Problem

A solid-state imaging device according to one embodiment of the present invention includes a light receiving section, N readout lines, a signal output section, and a vertical shift register. The light receiving section has a plurality of pixels including photodiodes, and the pixels are two-dimensionally arrayed in M rows and N columns. That is, the light receiving section has a plurality of pixels two-dimensionally arrayed so that the light receiving section has M rows and N columns. The N readout lines are disposed for the respective columns, and connected with the photodiodes included in the pixels of the respective columns via readout switches. The signal output section outputs a voltage value according to an amount of charge input through each of the readout lines. The vertical shift register controls an opening and closing operation of the readout switch for each of the rows. In this solid-state imaging device, a contour between one side of the light receiving section extending along a row direction and a pair of sides of the light receiving section extending along a column direction has a stepped shape. That is, the light receiving section has a stepped contour between an edge extending along the row direction and a pair of edges extending along the column direction. Moreover, this solid-state imaging device includes a dummy photodiode region formed along the stepped contour of the light receiving section.

In the above-described solid-state imaging device, by providing the contour between one side along the row direction of the light receiving section and a pair of sides along the column direction (typically, the contour of a part corresponding to corners of the light receiving section) in a stepped shape, when producing the solid-state imaging device from a substantially circular semiconductor wafer, the solid-state imaging device can be produced with an area larger than that of a rectangle that inscribes the circle. Therefore, according to the above-described solid-state imaging device, the light receiving section of a larger area can be obtained under limitations due to the size of the semiconductor wafer to serve as material.

Moreover, when a part of the contour of the light receiving section is provided in a stepped shape as described above, even after the solid-state imaging device is cut out of the semiconductor wafer, a relatively large space remains between the stepped part and the edge of the semiconductor wafer. When light is made incident into such a space, and unnecessary carriers are generated to flow in the light receiving section, noise is superimposed onto the pixels of the light receiving section close to the stepped contour part. Moreover, since such carriers move in various directions, unevenness is likely to occur in characteristics of the pixels of the light receiving section close to the stepped contour part, which leads to degradation in the uniformity of characteristics of the light receiving section. To address to such problems, in the above-described solid-state imaging device, the dummy photodiode region is formed along the stepped contour of the light receiving section. Thereby, unnecessary carriers generated in the periphery of the stepped light receiving section can be eliminated in this dummy photodiode region. Therefore, according to the above-described solid-state imaging device, flowing of unnecessary carriers into the light receiving section can be prevented, noise can be reduced, and degradation in uniformity of the light receiving section can be suppressed.

In one embodiment, the light receiving section may be configured such that L (L≧2) row groups each of which includes a plurality of rows having the same quantity of columns and arranged in the column direction. That is, in one embodiment, the light receiving section may include L row groups that are arrayed in the column direction and include a plurality of rows. In each of the row groups, a plurality of rows included in that row group may have the same quantity of pixels as each other. The stepped contour of the light receiving section may be realized by quantities of columns $N_{L-LA+1}$ to $N_L$ of a consecutive LA (where 2≦LA<L) row groups including a row group that has a quantity of columns $N_L$, and is located at one end in the column direction out of the L row groups satisfying $N_L<N_{L-1}<\ldots<N_{L-LA+1}$. Thus, by reducing the quantities of columns of the row groups as the row groups approach the end of the light receiving section, the stepped contour of the light receiving section can be suitably formed.

In one embodiment, the vertical shift register may be disposed along an end column of each of the L row groups, and at least a part of the dummy photodiode region may be formed between respective parts of the vertical shift register corresponding to respective row groups of the light receiving section and the row groups. Since the unnecessary carriers described above may be generated also in the vertical shift register, by thus arranging at least a part of the dummy photodiode region between the vertical shift register and the respective row groups of the light receiving section, unnecessary carriers to flow into the light receiving section can be more reliably eliminated.

In one embodiment, the solid-state imaging device may be characterized by further including a trunk line provided extending along the column direction of the light receiving section to supply signals and electrical power to respective parts of the vertical shift register corresponding to respective row groups of the light receiving section, in which at least a part of the dummy photodiode region is formed along both sides of the trunk line. Alternately, in one embodiment, the solid-state imaging device may be characterized by further including a trunk line provided extending along the column direction of the light receiving section to supply signals and electrical power to respective parts of the vertical shift register corresponding to respective row groups of the light receiving section, in which the dummy photodiode region is formed in a region except immediately under the trunk line.

Thus, by forming the dummy photodiode region on both sides of the trunk line provided extending along the column direction to supply signals and electrical power to the vertical shift register, or in a region except directly under the trunk line, and by not forming the dummy photodiode region between the trunk line and substrate, the interval between the trunk line and the dummy photodiode region can be sufficiently secured to suppress an increase in parasitic capacitance of the line. Particularly, in a large-area solid-state imaging device, since the length of the trunk line is elongated because of the large area, and a signal delay is likely to occur, such a device can be applied. Further, in the area where the contour of the light receiving section has a stepped shape, since the respective parts of the vertical shift register corresponding to the respective row groups of the light receiving section separate from each other, and the trunk line is also elongated, such effects are remarkable.

It should be noted that the trunk line in the present invention refers to, among the lines to supply signals and electrical power to the vertical shift register, a line (or line group) common to a plurality of parts included in the vertical shift register, and lines extending to the respective parts of the vertical shift register having branched off from the common line are not included therein.

In one embodiment, the solid-state imaging device may further includes a plurality of buffer amplifiers corresponding to respective row groups of the light receiving section, in which the trunk line and the parts of the vertical shift register are connected via the buffer amplifiers, respectively. As described above, in the area where the contour of the light receiving section has a stepped shape, the trunk line is elongated. The elongated trunk line results in a capacitance load, which easily causes a signal delay. Further, when the trunk line is directly wired to all shift register parts of the vertical shift register, wiring is carried out for a very large number of gate switches from the single trunk line, and this leads to an increase in capacitance load, and a signal delay more easily occurs. In such a case, by connecting the respective parts of the vertical shift register corresponding to the respective row groups of the light receiving section and the trunk line via the buffer amplifiers, the effect of parasitic capacitance can be effectively suppressed, and a capacitance load to the trunk line can be reduced by reducing the number of gates that are driven directly from the trunk line, so that a signal delay can be made unlikely to occur.

In one embodiment, the solid-state imaging device may be characterized in that the dummy photodiode region has the same semiconductor layer structure as that of the photodiode. Thereby, the dummy photodiode region may be easily formed without adding a special process when producing the solid-state imaging device.

Advantageous Effects of Invention

According to the solid-state imaging device of the present invention, a light receiving section of a larger area can be obtained under limitations due to the size of a semiconductor wafer to serve as material.

shows a state where the solid-state imaging device 1 of the present embodiment is arranged.

Figure 8:
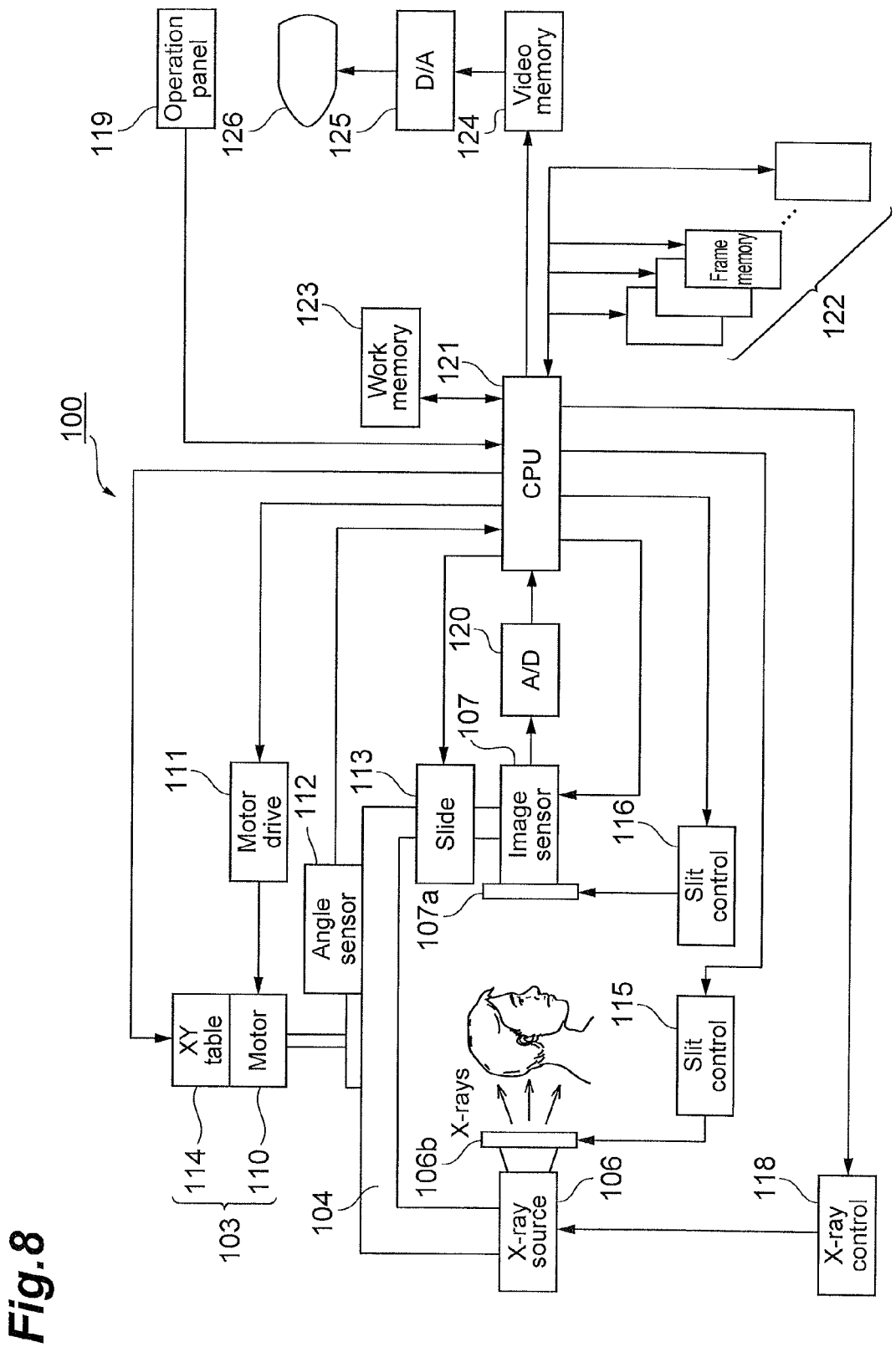

FIG. 8 is a configuration diagram of an X-ray CT apparatus 100 according to one embodiment.

DESCRIPTION OF EMBODIMENTS

Hereinafter, embodiments of a solid-state imaging device according to the present invention will be described in detail with reference to the accompanying drawings. The same components will be denoted with the same reference symbols in the description of the drawings, and overlapping description will be omitted.

Figure 1:
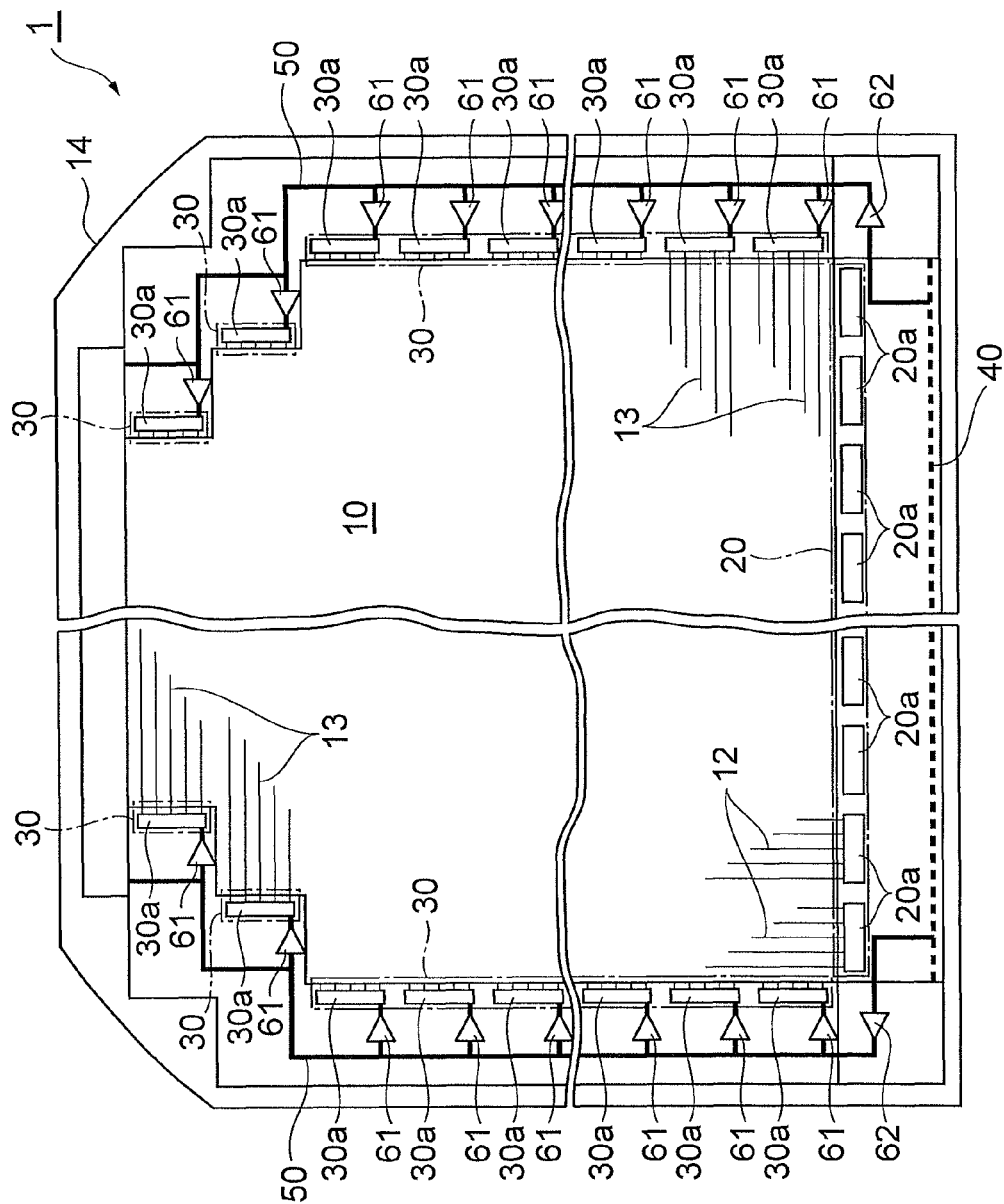
FIG. 1 illustrates a schematic configuration of a solid-state imaging device 1 according to one embodiment of the present invention.

A solid-state imaging device 1 according to an embodiment of the present invention is used for a so-called passive CMOS image sensor, and is a semiconductor element for which a plurality of pixels are two-dimensionally arranged. As shown in FIG. 1, the solid-state imaging device 1 according to the present embodiment includes a light receiving section 10, a signal output section 20 including a plurality of output parts 20a, and a vertical shift register 30 including a plurality of shift register parts 30a. The light receiving section 10, the signal output section 20, and the vertical shift register 30 are built in the main surface of a semiconductor substrate 14 such as, for example, a silicon substrate. In addition, this semiconductor substrate 14 may be bonded to a base member having a flat-plate shape to maintain mechanical strength.

Figure 2:
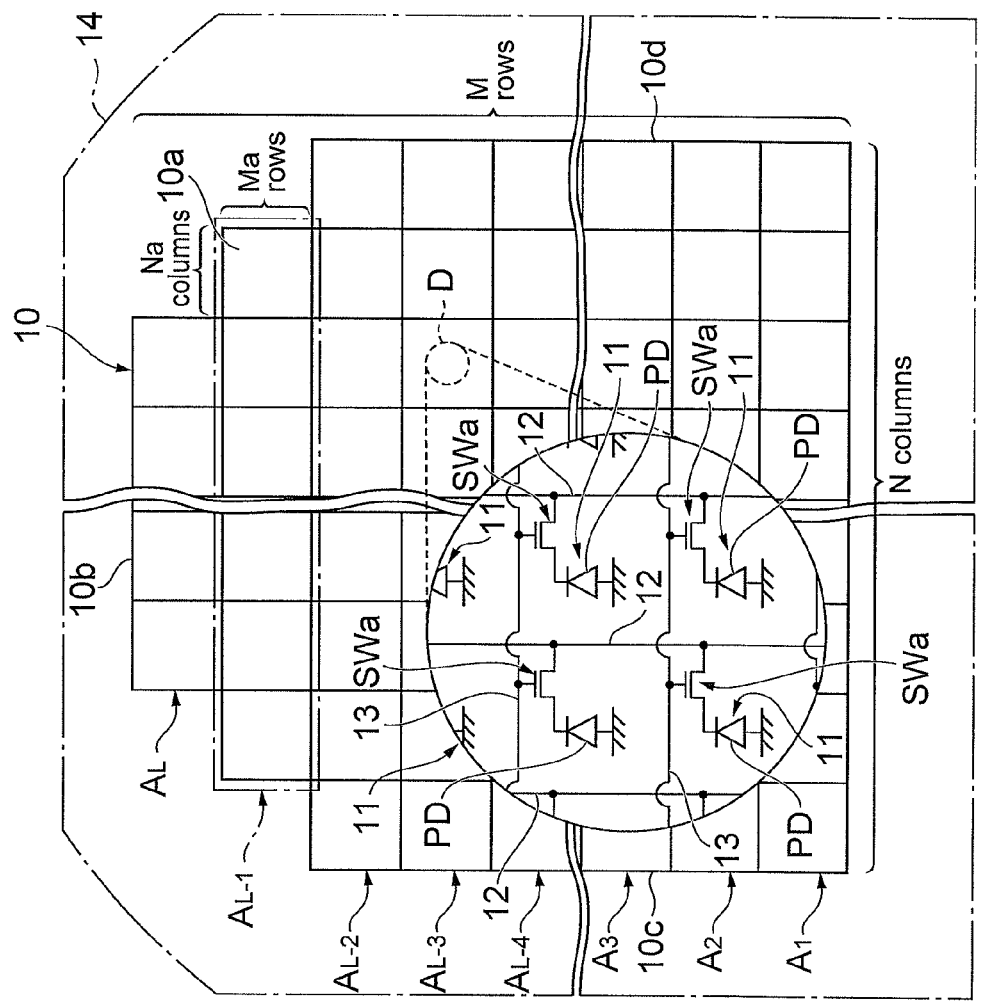
FIG. 2 is a view showing a configuration of a light receiving section 10 included in the solid-state imaging device 1. In the same figure, a region D of a part of the light receiving section 10 is shown in an enlarged manner.

Referring to FIG. 2, the light receiving section 10 is configured by two-dimensionally arranging the plurality of pixels 11 in M rows and N columns (M and N are each an integer not less than 2). That is, the light receiving section 10 has a plurality of pixels 11 two-dimensionally arrayed so that the light receiving section 10 has M rows and N columns. The light receiving section 10 of the present embodiment is configured such that L (L≧2) row groups $A_1$ to $A_L$ each having a plurality of rows that have the same number or quantity of columns are arranged in the column direction. That is, the light receiving section 10 includes L row groups $A_1$ to $A_L$ which are arrayed in the column direction and each of which has a plurality of pixel rows. In each of the row groups $A_1$ to $A_L$, a plurality of rows contained in that row group have the same number or quantity of pixels as each other. Each of the row groups $A_1$ to $A_L$ is configured with a plurality of pixel groups 10a arranged in the row direction, as the range of a row group $A_{L-1}$ is shown by an alternate long and short dashed line in FIG. 2, for example. Each of the pixel groups 10a is configured with a plurality of pixels 11 two-dimensionally arrayed in Ma rows and Na columns (2≦Ma<M, 2≦Na<N). The pixel group 10a is a unit of exposure when producing the light receiving unit 10 by a photolithography technique.

Moreover, in the light receiving section 10 of the present embodiment, quantities of columns $N_{L-LA+1}$ to $N_L$ of a consecutive LA (where 2≦LA<L) row groups $A_{L-LA+1}$ to $A_L$ including a row group $A_L$ that has a quantity of columns $N_L$ and is located at one end in the column direction out of the L row groups $A_1$ to $A_L$ satisfies $N_L<N_{L-1}<\ldots<N_{L-LA+1}$, so that a contour between one side 10b along the row direction of the light receiving section 10 and a pair of sides 10c and 10d along the column direction thereof has a stepped shape.

Specifically, description will be given of the case with LA=3. In FIG. 2, the number of pixel groups 10a contained in the row group $A_L$ located at one end in the column direction out of the L row groups $A_1$ to $A_L$ is provided as n. In this case, the number of columns $N_L$ of the pixels 11 contained in the row group $A_L$ is $N_L=n\times Na$. Next, the number of pixel groups 10a contained in the row group $A_{L-1}$ adjacent to the row group $A_L$ is increased by one each at both ends as compared with that of the row group $A_L$ to be (n+2). Therefore, the number of columns $N_{L-1}$ of the pixels 11 contained in the row group $A_{L-1}$ is $N_{L-1}=(n+2)\times Na$. Likewise, the number of pixel groups 10a contained in the row group $A_{L-2}$ is (n+4), and the number of columns $N_{L-2}$ of the pixels 11 contained in the row group $A_{L-2}$ is $N_{L-2}=(n+4)\times Na$. The number of pixel groups 10a contained in the respective row groups $A_{L-2}$ to $A_1$ from the row group $A_{L-2}$ to the row group $A_1$ of the other end is constant, and the numbers or quantities of columns $N_{L-2}$ to $N_1$ of the pixels 11 contained in these row groups $A_{L-2}$ to $A_1$ are all equal, (n+4)×Na.

Thus, in the light receiving section 10 shown in FIG. 2, the respective quantities of columns $N_{L-2}$ to $N_L$ of the three consecutive row groups $A_{L-2}$ to $A_L$ including the row group $A_L$ located at one end in the column direction are increased in order from the side of the row group $A_L$, and satisfy a relationship of $N_L<N_{L-1}<N_{L-2}$. Further, in the solid-state imaging device 1 of the present embodiment, as a result of the quantities of columns of the pixels 11 contained in the row groups $A_{L-2}$ to $A_L$ being thus set, the contour of the light receiving section 10 defined by the row groups $A_{L-2}$ to $A_L$, that is, the contour between the side 10b and the sides 10c and 10d of the light receiving section 10, has a stepped shape.

The pixels 11 of the light receiving section 10 are of the PPS type, and have a common configuration. That is, each of the pixels 11 includes a photodiode PD and a readout switch SWa. The anode terminal of the photodiode PD is grounded, and the cathode terminal of the photodiode PD is connected to a readout line 12 via the readout switch SWa. The photodiode PD generates charge of an amount according to an incident light intensity, and accumulates the generated charge in a junction capacitance section. The readout switch SWa is supplied with a row selection control signal via a row selection line 13. The row selection control signal is a signal that instructs an opening and closing operation of the readout switches SWa of the pixels 11 included in the respective rows of the light receiving section 10.

In each of the pixels 11, when the row selection control signal is at low (L) level, the readout switch SWa opens, and a charge generated in the photodiode PD is not output to the readout line 12 but is accumulated in the junction capacitance section. On the other hand, when the row selection control signal is at high (H) level, the readout switch SWa closes, and the charge generated in the photodiode PD and accumulated in the junction capacitance section until then is output to the readout line 12 through the readout switch SWa.

Referring again to FIG. 1, the vertical shift registers 30 are disposed at both ends of the light receiving section 10 in the row direction. The vertical shift register 30 is provided for controlling charge outputs from the pixels 11 shown in FIG. 2 for each of the rows, and supplies row selection control signals to the respective pixels 11 via the row selection lines 13. The vertical shift register 30 is configured with a plurality of shift register parts 30a provided in association with the L row groups $A_1$ to $A_L$ described above. In the present embodiment, L shift register parts 30a are arranged at one end side of the row groups $A_1$ to $A_L$ in the row direction, and other L shift register parts 30a are disposed at the other end side. Each of the respective shift register parts 30a is arranged along the end column of the corresponding row group, and connected to Ma row selection lines 13 of that row group.

The signal output section 20 is arranged adjacent to one side (specifically, one side defined by the row group $A_1$) of the light receiving section 10 extending along the row direction. The signal output section 20 is connected with readout lines 12 disposed in association with the respective columns of the light receiving section 10, and outputs voltage values (analog or digital values) according to the amounts of charge input through the readout lines 12. The signal output section 20 is configured with a plurality of output parts 20a provided in association with a plurality of pixel groups 10a that form the row group $A_1$ described above. The respective output parts 20a are connected to Na readout lines 12 of corresponding pixel groups 10a, respectively.

The solid-state imaging device 1 of the present embodiment, as shown in FIG. 1, further includes a plurality of terminal electrodes 40. The terminal electrodes 40 are arranged in an edge portion of the semiconductor substrate 14 along the signal output section 20, for example. Some of the terminal electrodes 40 are connected to the signal output section 20, and are input with a reset signal to reset an integration circuit included in the signal output section 20, a hold signal to control signal input to a holding circuit included in the signal output section 20, a horizontal start signal to start operation of a horizontal shift register included in the signal output section 20, a horizontal clock signal that defines a clock of the horizontal shift register, and a supply voltage to drive the signal output section 20 from outside of the solid-state imaging device 1, and output a voltage signal output from the signal output section 20 to the outside of the solid-state imaging device 1.

Some other of the terminal electrodes 40 are connected to the respective shift register parts 30a of the vertical shift register 30 via a trunk line 50. These terminal electrodes 40 are input with a gate signal, a vertical start signal, a vertical clock signal, and a supply voltage to drive the respective shift register parts 30a, respectively, to be used in the vertical shift register 30, for example.

The trunk line 50 is a line group including a plurality of lines provided extending along the column direction of the light receiving section 10 in order to supply signals and electrical power to the respective shift register parts 30a corresponding to the respective row groups $A_1$ to $A_L$ of the light receiving section 10. The trunk line 50 in the present embodiment refers to, out of the lines to supply signals and electrical power to the vertical shift register 30, a line (or line group) common to a plurality of parts included in the vertical shift register 30, and lines extending to the respective shift register parts 30a of the vertical shift register 30 having branched off from the common line are not included therein. In addition, the solid-state imaging device 1 includes a plurality of buffer amplifiers 61 provided corresponding to the respective row groups $A_1$ to $A_L$, and the trunk line 50 and the respective shift register parts 30a may be connected to each other via corresponding buffer amplifiers 61, respectively. Moreover, a buffer amplifier 62 may be connected between the terminal electrode 40 and the trunk line 50.

Figure 3:
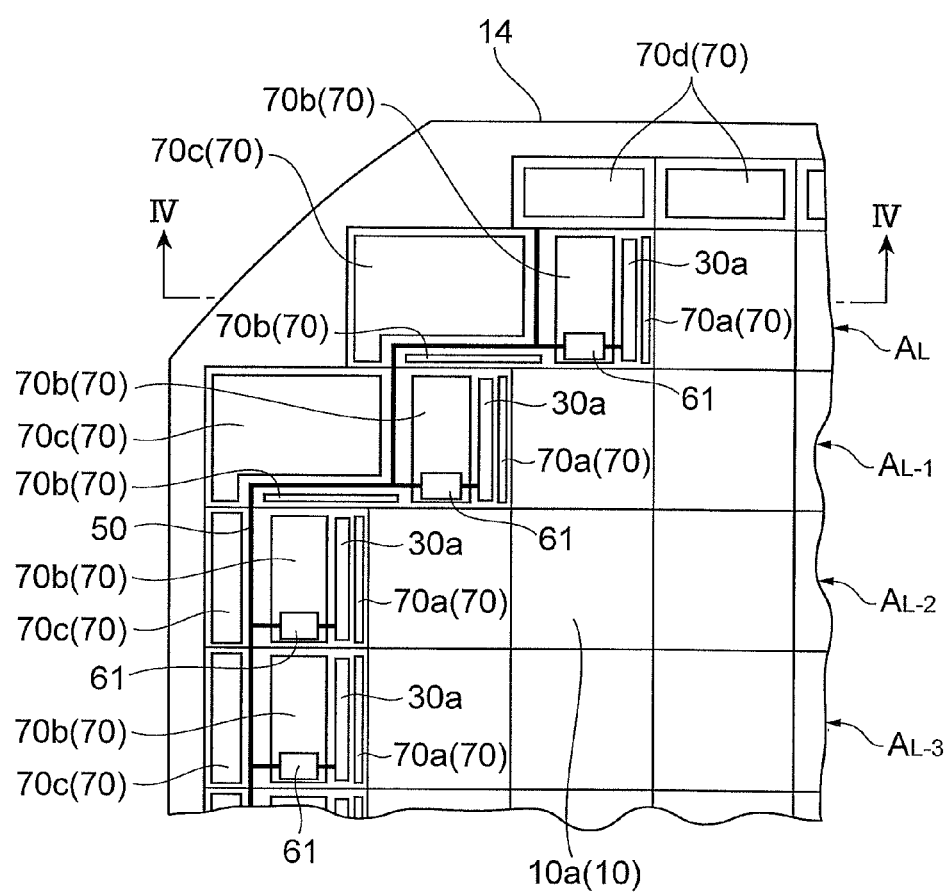
FIG. 3 is a plan view showing a peripheral configuration of a stepped contour part of the light receiving section 10.

Here, the peripheral configuration of a part where the contour has a stepped shape in the light receiving section 10 will be further described. FIG. 3 is a plan view showing a peripheral configuration of that part, and FIG. 4 is a side sectional view showing the main part of a section along a line IV-IV of FIG. 3.

Figure 4:
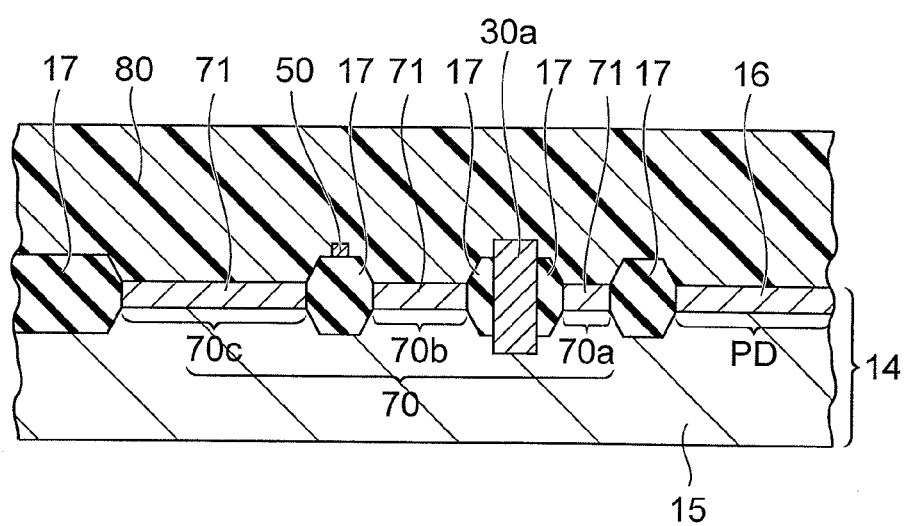
FIG. 4 is a side sectional view showing the main part of a section along a line IV-IV of FIG. 3.

As shown in FIG. 3 and FIG. 4, the solid-state imaging device 1 further includes a dummy photodiode region 70 in addition to the above-described configuration. The dummy photodiode region 70 is a region to absorb light incident outside of the light receiving section 10 and eliminate generated carriers, and is formed mainly along the stepped contour of the light receiving section 10.

The dummy photodiode region 70 has the same semiconductor layer structure as that of the photodiodes PD of the respective pixels 11. Specifically, as shown in FIG. 4, the photodiodes PD of the respective pixels 11 have a second conductivity-type (for example, n-type) semiconductor layer 16 being an ion injection layer, formed on the surface side of a first conductivity-type semiconductor region 15 having a first conductivity type (for example, p-type) and to serve as a base of the semiconductor substrate 14. The second conductivity-type semiconductor layer 16 and the first conductivity-type semiconductor region 15 form a p-n junction with each other, and the second conductivity-type semiconductor layer 16 serves as a light detecting region on which an image of light is made incident to generate charge (carriers). The second conductivity-type semiconductor layers 16 of the respective pixels 11 are isolated from each other by an oxide film (LOCOS; Local Oxidation of Silicon) 17.

The dummy photodiode region 70 is also the same in configuration as the photodiode PD, and has a second conductivity-type semiconductor layer 71 being an ion injection layer formed on the surface side of the first conductivity-type semiconductor region 15. The second conductivity-type semiconductor layer 71 and the first conductivity-type semiconductor region 15 form a p-n junction with each other, and when light and radiation made incident on the surroundings of the light receiving section 10 are made incident onto the second conductivity-type semiconductor layer 71, a charge is generated. The second conductivity-type semiconductor layer 71 is connected to a reference potential (ground potential) via an electrode included in a plurality of terminal electrodes 40, for example, and a generated charge is discharged to the outside as unnecessary carriers via that electrode.

In addition, the respective pixels 11 of the light receiving section 10 and the dummy photodiode region 70, and further the respective components on the semiconductor substrate 14 excluding the terminal electrodes 40, such as the signal output section 20, the vertical shift register 30, and the trunk line 50 are covered with a passivation film 80 shown in FIG. 4, and protected.

The dummy photodiode region 70 having such a configuration includes, as shown in FIG. 3, partial regions 70a, partial regions 70b, partial regions 70c, and partial regions 70d. A plurality of partial regions 70a are formed between the respective shift register parts 30a corresponding to the respective row groups $A_1$ to $A_L$ of the light receiving section 10 and the row groups $A_1$ to $A_L$, respectively, and the respective partial regions 70a extend along the end columns of the respective row groups $A_1$ to $A_L$. As shown in FIG. 4, the photodiodes PD in the end columns of the respective row groups $A_1$ to $A_L$ and the partial regions 70a, and the respective shift register parts 30a and the partial regions 70a are separated from each other by the oxide films 17 provided therebetween, respectively.

A plurality of partial regions 70b are formed mainly between the respective shift register parts 30a and the trunk line 50, respectively, and the respective partial regions 70b are provided extending along an inner edge of the trunk line 50 when viewed from the direction vertical to a substrate plane of the semiconductor substrate 14. Here, a part of the trunk line 50 extending along one-side ends of the row groups $A_1$ to $A_{L-2}$, that is, a linear contour of the light receiving section 10 extends straight along the column direction. On the other hand, for a part extending along one-side ends of the row groups $A_{L-1}$ to $A_L$, that is, a stepped contour of the light receiving section 10, a part extending in the row direction and a part extending in the column direction are alternately linked, so that the trunk line 50 also shows a stepped shape. The partial region 70b is formed not only in a region along apart extending in the column direction of the trunk line 50, but also in a region along a part extending in the row direction.

Each of the plurality of partial regions 70c is formed along an edge at the outside (that is, the side opposite to where the partial regions 70b are formed) of the trunk line 50. The partial regions 70c have their shapes and areas greatly different from each other, depending on the corresponding row groups. That is, the partial regions 70c corresponding to the row groups $A_1$ to $A_{L-2}$ that form a linear contour of the light receiving section 10 extend along the trunk line 50 extending in the column direction, and have an elongated shape having its longitudinal direction in the column direction in a relatively narrow region between an edge of the semiconductor substrate 14 and the trunk line 50. On the other hand, the partial regions 70c corresponding to the row groups $A_{L-1}$ to $A_L$ that form a stepped contour of the light receiving section 10 extend along both of the part extending in the row direction of the trunk line 50 and the part extending in the row direction, and has a wide shape having its longitudinal direction in the row direction in a relatively wide region between the edge of the semiconductor substrate 14 and the trunk line 50.

In addition, the partial regions 70b and 70c described above are formed along both sides of the trunk line 50, and not formed directly under the trunk line 50. Directly under the trunk line 50, there is formed an oxide film 17 as shown in FIG. 4, and the trunk line 50 and the first conductivity-type semiconductor region 15 are insulated from each other by this oxide film 17. The oxide film 17 is formed thicker than the second conductivity-type semiconductor layer 71 of the dummy photodiode region 70, and parasitic capacitance of the trunk line 50 is reduced by sufficiently securing the distance between the trunk line 50 and the first conductivity-type semiconductor region 15. However, the branch lines extending from the trunk line 50 via the buffer amplifiers 61 to the shift register parts 30a are partially formed on the second conductivity-type semiconductor layer 71 that forms the partial region 70b since the effect of parasitic capacitance is negligible.

A plurality of partial regions 70d are arranged along one side, of a pair of sides of the light receiving section 10 extending along the row direction, opposite to the side along which the signal output section 20 is provided, and are respectively provided adjacent to a plurality of pixel groups 10a that form the row group $A_L$.

In addition, the arrangement of the partial regions 70a to 70d described above is simply realized, when forming the shift register parts 30a etc., at both ends of the respective row groups $A_1$ to $A_L$ by a photolithography technique, by simultaneously forming the partial regions 70a to 70d one each for each of the unit regions of exposure.

Figure 5:
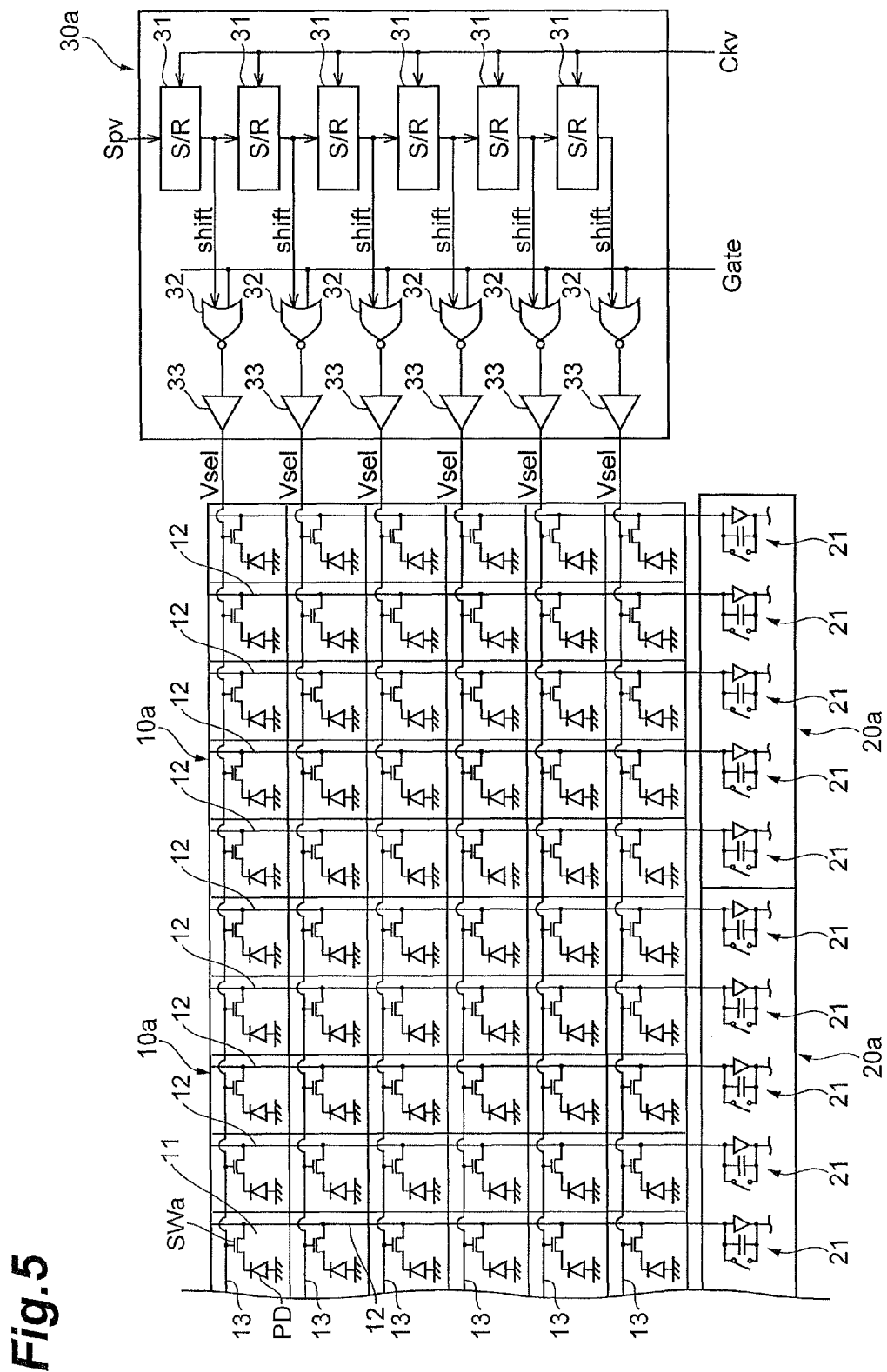
FIG. 5 is a circuit diagram showing in greater detail a configuration of two pixel groups 10a included in a certain row group of the light receiving section 10 and a configuration of a shift register part 30a corresponding to the row group.

Then, a detailed configuration of the light receiving section 10, the signal output section 20, and the vertical shift register 30 will be described. FIG. 5 is a circuit diagram showing in greater detail a configuration of two pixel groups 10a included in a certain row group of the light receiving section 10 and a configuration of a shift register part 30a corresponding to that row group.

The shift register part 30a includes a plurality of shift registers 31 mutually connected in series, and NOR circuits (NOR gates) 32 and buffers 33 provided corresponding to the respective rows contained in the row group of the light receiving section 10. To each of the shift registers 31, a vertical clock signal Ckv that defines operation clocks of the respective shift registers 31 is supplied via the trunk line 50 (refer to FIG. 1). Moreover, to one end of a series circuit including the shift registers 31, a vertical start signal Spy to start operation of the vertical shift register 30 is supplied via the trunk line 50.

When the vertical start signal Spy is input to the shift register 31 located at the first stage, output voltages Shift of the shift registers 31 fall in order only for a fixed period in line with the timing of the vertical clock signal Ckv. Then, the output voltages Shift of the respective shift registers 31 are input in order to the NOR gates 32 provided for each of the rows, and logical NORs with a gate signal Gate are output to the buffers 33, respectively. Signal outputs from the buffers 33 are provided to the row selection lines 13 as row selection control signals Vsel, respectively. It should be noted that the gate signal Gate is a signal to reduce the time width of a pulse included in the row selection control signal Vsel.

Moreover, as shown in FIG. 5, output terminals of the respective Ma pixels 11 that configures each row of the pixel group 10a are connected, via the readout line 12, to the output part 20a corresponding to the pixel group 10a (concretely, integration circuits 21 provided for each of the columns in the output parts 20a).

Figure 6:
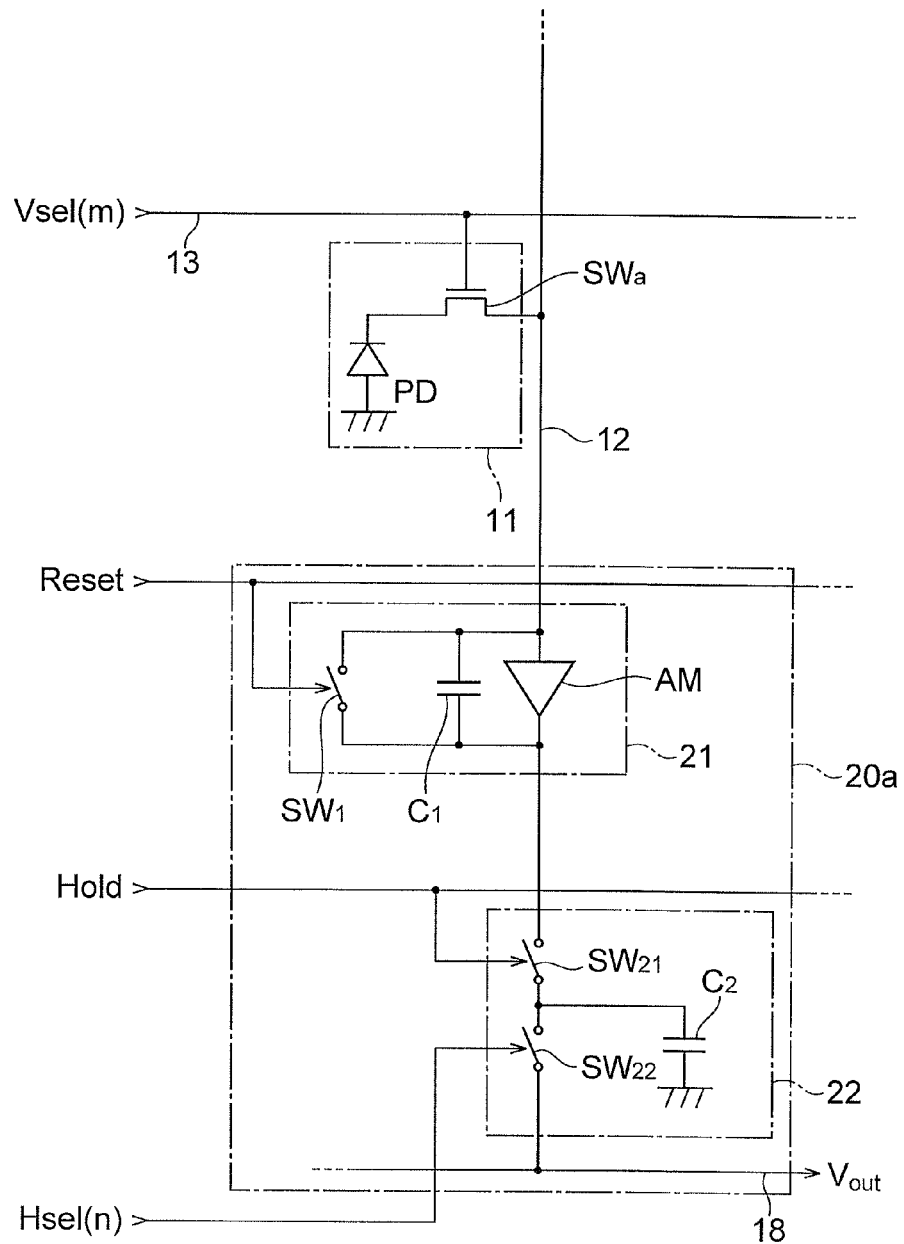
FIG. 6 is a circuit diagram showing a concrete configuration of circuits connected to each readout line 12 in an output part 20a of a signal output section 20.

FIG. 6 is a circuit diagram showing a concrete configuration of circuits connected to each readout line 12 in an output part 20a of the signal output section 20. In FIG. 6, a circuit configuration of the output part 20a corresponding to a single readout line 12 is shown.

As shown in FIG. 6, the output part 20a has an integration circuit 21 and a holding circuit 22 provided for each of the readout lines 12. The integration circuit 21 includes an amplifier AM, an integrating capacitive element $C_1$, and a discharge switch $SW_1$. The integrating capacitive element $C_1$ and the discharge switch $SW_1$ are connected in parallel to each other, and provided between an input terminal and an output terminal of the amplifier AM. The input terminal of the amplifier AM is connected with the corresponding readout line 12. The discharge switch $SW_1$ is supplied with a discharge control signal Reset from a control circuit (not shown). The discharge control signal Reset is a signal that controls collectively an opening and closing operation of the discharge switch $SW_1$ of each of the integration circuits 21 included in the output part 20a.

In this integration circuit 21, when the discharge control signal Reset is at high level, the discharge switch $SW_1$ closes, the integrating capacitive element $C_1$ is discharged, and a voltage value to be output from the integration circuit 21 is initialized. When the discharge control signal Reset is at low level, the discharge switch $SW_1$ opens, a charge input to the input terminal is accumulated in the integrating capacitive element $C_1$, and a voltage value according to the accumulated charge amount is output from the integration circuit 21.

The holding circuit 22 includes an input switch $SW_{21}$, an output switch $SW_{22}$, and a holding capacitive element $C_2$. One end of the holding capacitive element $C_2$ is grounded. The other end of the holding capacitive element $C_2$ is connected with the output terminal of the integration circuit 21 via the input switch $SW_{21}$, and connected with a voltage output line 18 via the output switch $SW_{22}$. The input switch $SW_{21}$ is supplied with a hold control signal Hold from the control circuit (not shown). The hold control signal Hold is a signal that controls collectively an opening and closing operation of the input switch $SW_{21}$ of each of the holding circuits 22 included in the output part 20a. Moreover, the output switch $SW_{22}$ is supplied with an n-th column selection control signal Hsel(n) from the control circuit (not shown). The n-th column selection control signal Hsel(n) is a signal that controls for each of the columns an opening and closing operation of the output switch $SW_{22}$ included in the holding circuit 22.

In this holding circuit 22, when the hold control signal Hold switches from high level to low level, the input switch $SW_{21}$ switches from a closed state to an open state, and a voltage value being input to the input terminal at this time is held in the holding capacitive element $C_2$. Moreover, when the n-th column selection control signal Hsel(n) is at high level, the output switch $SW_{22}$ closes, and the voltage value held in the holding capacitive element $C_2$ is output to the voltage output line 18.

Advantageous effects to be obtained by the solid-state imaging device 1 of the present embodiment described above will be described. In the solid-state imaging device 1, the arrangement of the pixel groups 10a contained in the light receiving section 10 are devised, so that the contour between one side 10b along the row direction of the light receiving section 10 and a pair of sides 10c and 10d along the column direction (that is, the contour of a part equivalent to two corners of the rectangular light receiving section 10) has a stepped shape.

Figure 7:
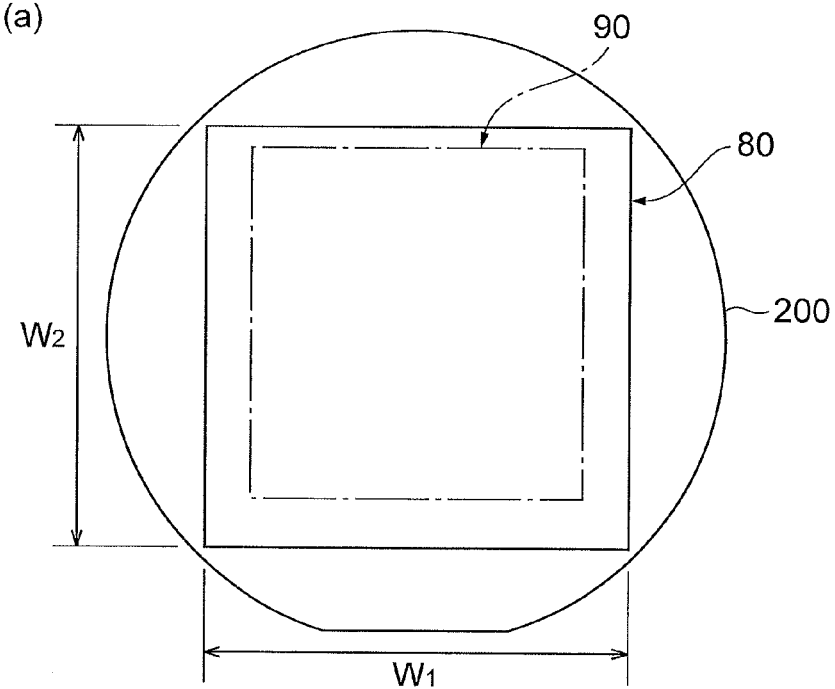
FIG. 7 are views showing states where a solid-state imaging device is arranged on a substantially circular semiconductor wafer 200, wherein the area (a) shows a state where a conventional solid-state imaging device 80 including a rectangular light receiving section 90 is formed, and the area (b)
Figure 7:
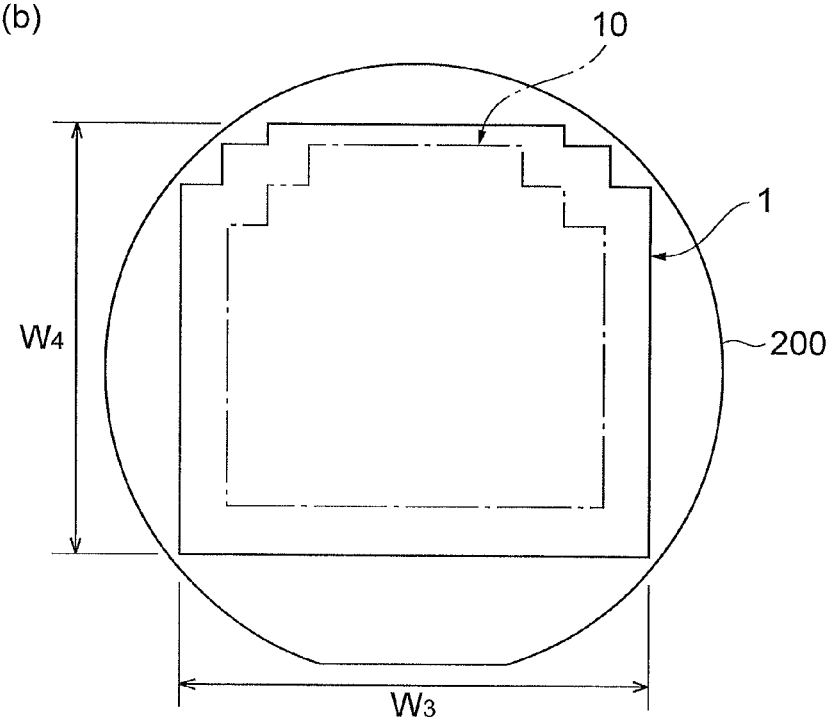

Here, FIG. 7 are views showing states where a solid-state imaging device is arranged on a substantially circular semiconductor wafer 200, in which a state where a conventional solid-state imaging device 80 with a rectangular light receiving section 90 is arranged is shown in the area (a) of FIG. 7, and a state where the solid-state imaging device 1 of the present embodiment is arranged is shown in area (b) of FIG. 7. A solid-state imaging device is generally cut out by dicing of the substantially circular semiconductor wafer 200 as shown in FIG. 7, but as shown in the area (a) of FIG. 7, in the case of a solid-state imaging device 80 with the rectangular light receiving section 90, for obtaining as large a semiconductor area as possible, the outline of the solid-state imaging device 80 results in a rectangular shape (a width $W_1$ in the row direction, a width $W_2$ in the column direction) that inscribes an outer edge of the substantially circular semiconductor wafer 200. On the other hand, as shown the area (b) of FIG. 7, in the solid-state imaging device 1 of the present embodiment, as a result of providing the contour of two corners of the light receiving section 10 in a stepped shape, the contour of a corresponding part of the solid-state imaging device 1 also results in a stepped shape, the solid-state imaging device 1 can be provided with a width $W_3$ in the row direction and a width $W_4$ in the column direction that are longer than the widths $W_1$ and $W_2$, respectively, and even in consideration of the area of the part cut away in a stepped shape, the light receiving section 10 can be provided with a larger area.

Thus, by the solid-state imaging device 1 of the present embodiment, the light receiving section 10 of a larger area can be obtained under limitations due to the size of the semiconductor wafer 20 to serve as material.

Moreover, when a part of the contour of the light receiving section 10 is provided in a stepped shape as described above, even after the solid-state imaging device 1 is cut out of the semiconductor wafer 200, a relatively large space remains between the stepped part and the edge of the semiconductor substrate 14. When light is made incident into such a space, and unnecessary carriers are generated to flow in the light receiving section 10, noise is superimposed onto the pixels 11 of the light receiving section 10 close to the stepped contour part. Moreover, since such carriers move in various directions, and the size of a neighboring space is also not uniform for each of the pixels 11, unevenness is likely to occur in characteristics of the pixels 11 of the light receiving section 10 close to the stepped contour part, which leads to degradation in the uniformity of characteristics of the light receiving section 10.

To address such problems, in the solid-state imaging device 1 of the present embodiment, the dummy photodiode region 70 is formed along the stepped contour of the light receiving section 10. Thereby, unnecessary carriers generated in the periphery of the stepped light receiving section 10 can be eliminated in this dummy photodiode region 70. Therefore, by the solid-state imaging device 1 of the present embodiment, flowing of unnecessary carriers into the light receiving section 10 can be prevented, noise can be reduced, and degradation in uniformity of the light receiving section 10 can be suppressed.

Moreover, as in the present embodiment, the light receiving section 10 is configured such that L (L≧2) row groups $A_1$ to $A_L$ each having a plurality of pixel rows are arranged in the column direction, and the stepped contour of the light receiving section 10 may be realized by the quantities of columns $N_{L-LA+1}$ to $N_L$, of the consecutive LA (2≦LA<L) row groups $A_{L-LA+1}$ to $A_L$ including the row group $A_L$ (number or quantity of columns of $N_L$) located at one end in the column direction out of the L row groups $A_1$ to $A_L$ satisfying $N_L < N_{L-1} < \ldots < N_{L-LA+1}$. Thus, by reducing the quantities of columns of the row groups as they approach the end of the light receiving section 10, the stepped contour of the light receiving section 10 can be suitably formed.

Moreover, as in the present embodiment, when the vertical shift register 30 is disposed along the end column of each of the L row groups $A_1$ to $A_L$, the partial regions 70a of the dummy photodiode region 70 may be formed between the respective shift register parts 30a of the vertical shift register 30 and the corresponding respective row groups $A_1$ to $A_L$. Since the unnecessary carriers described above can be generated also in the vertical shift register 30, by thus arranging the partial regions 70a of the dummy photodiode region 70, unnecessary carriers to flow into the light receiving section 10 can be more reliably eliminated.

Moreover, as in the present embodiment, when the trunk line 50 to supply signals and electrical power to the respective parts of the vertical shift register 30 corresponding to the respective row groups of the light receiving section 10 is provided extending along the column direction of the light receiving section 10, the partial regions 70b and 70c of the dummy photodiode region 70 may be formed along both sides of the trunk line 50, that is, formed in a region except directly under the trunk line 50. Thus, by forming the dummy photodiode region 70 on both sides of the trunk line 50, or in a region except directly under the trunk line 50, and by not forming the dummy photodiode region 70 in a region of the semiconductor substrate 14 directly under the trunk line 50, the interval between the trunk line 50 and the semiconductor substrate 14 can be sufficiently secured to suppress an increase in parasitic capacitance of the trunk line 50 and a signal delay involved. Particularly, in a large-area solid-state imaging device 1, since the length of the trunk line 50 is elongated because of the large area, and a signal delay is likely to occur, such a device can be applied. Further, in the area where the contour of the light receiving section 10 has a stepped shape, since the respective shift register parts 30a of the vertical shift register 30 corresponding to the respective row groups (in the present embodiment, $A_L$, $A_{L-1}$, and $A_{L-2}$) of the light receiving section 10 are separated from each other, and the trunk line 50 is also elongated, such effects are remarkable.

Moreover, as in the present embodiment, it is preferable that the trunk line 50 and the respective shift register parts 30a are connected via the buffer amplifiers 61 corresponding to the respective row groups $A_1$ to $A_L$ of the light receiving section 10. As described above, in the area where the contour of the light receiving section 10 has a stepped shape, the trunk line 50 is elongated. The elongated trunk line 50 serves as a capacitance load, which easily causes a signal delay. Further, when the trunk line 50 is directly wired to all shift register parts 30a of the vertical shift register 30, wiring is carried out for a very large number of gate switches from the single trunk line 50, and this leads to an increase in capacitance load, and a signal delay more easily occurs. In such a case, by connecting the respective shift register parts 30a of the vertical shift register 30 corresponding to the respective row groups $A_1$ to $A_L$ of the light receiving section 10 and the trunk line 50 via the buffer amplifiers 61, the effect of parasitic capacitance can be effectively suppressed, a capacitance load to the trunk line 50 can be reduced by reducing the number of gates that are driven directly from the trunk line 50, so that a signal delay can be made unlikely to occur.

Moreover, as in the present embodiment, the dummy photodiode region 70 may have the same semiconductor layer structure as that of the photodiodes PD of the respective pixels 11. Thereby, the dummy photodiode region 70 may be easily formed without adding a special process when producing the solid-state imaging device 1.

The solid-state imaging device 1 according to the present embodiment, as a result of a scintillator being provided at the front of the light receiving section 10, can be suitably used in an X-ray CT apparatus, for example. Therefore, an embodiment of an X-ray CT apparatus including the solid-state imaging device 1 according to the present embodiment will be described in the following.

FIG. 8 is a configuration diagram of an X-ray CT apparatus 100 according to the present embodiment. In the X-ray CT apparatus 100 shown in this figure, an X-ray source 106 generates X-rays toward a subject. The radiation field of X-rays generated from the X-ray source 106 is controlled by a primary slit plate 106b. The X-ray source 106 has a built-in X-ray tube, and by adjusting conditions of the X-ray tube, such as a tube voltage, a tube current, and energization time, the X-ray dose to the subject is controlled. An X-ray image sensor 107 is equivalent to the solid-state imaging device 1 according to the present embodiment, is provided with a scintillator panel at the front of its light receiving section 10, and images an X-ray image transmitted through the subject. In front of the X-ray image sensor 107, a secondary slit plate 107a that limits an X-ray incident region is provided.

A swing arm 104 holds the X-ray source 106 and the X-ray image sensor 107 so as to be opposed, and swings these around the subject in panoramic tomography. Moreover, in the case of linear tomography, a sliding mechanism 113 for linearly displacing the X-ray image sensor 107 with respect to the subject is provided. The swing arm 104 is driven by an arm motor 110 that forms a rotary table, and a rotation angle thereof is detected by an angle sensor 112. Moreover, the arm motor 110 is mounted on a movable portion of an XY table 114, and the center of rotation is arbitrarily adjusted in a horizontal plane.

Image signals output from the X-ray image sensor 107 are converted to, for example, 10-bit (=1024 level) digital data by an AD converter 120, once taken in a CPU (central processing unit) 121, and then stored in a frame memory 122. From the image data stored in the frame memory 122, a tomographic image along any tomographic plane is reproduced by a predetermined arithmetic processing. The reproduced tomographic image is output to a video memory 124, converted to analog signals by a DA converter 125, and then displayed by an image display section 126 such as a CRT (cathode ray tube), and provided for various diagnoses.

The CPU 121 is connected with a work memory 123 required for signal processing, and further connected with an operation panel 119 having a panel switch, an X-ray irradiation switch, etc. Moreover, the CPU 121 is connected to a motor drive circuit 111 that drives the arm motor 110, slit control circuits 115, 116 that control the opening range of the primary slit plate 106b and the secondary slit plate 107a, an X-ray control circuit 118 that controls the X-ray source 106, respectively, and further outputs a clock signal to drive the X-ray image sensor 107.

The X-ray control circuit 118 is capable of feedback-controlling the X-ray dose to the subject based on signals imaged by the X-ray image sensor 107.

The X-ray CT apparatus 100, as a result of including the solid-state imaging device 1 according to the present embodiment, can have a light receiving section of a larger area. Moreover, flowing of unnecessary carriers into the light receiving section can be prevented, noise can be reduced, and degradation in uniformity of the light receiving section can be suppressed.

The solid-state imaging device of the present invention is not limited to the above embodiment, and various other modifications can be made. For example, in the above-described embodiment, a configuration where vertical shift registers are arranged at both ends of a light receiving section in the row direction has been exemplified in the above-described embodiment, but also in a configuration where a vertical shift register is arranged at one of the ends, the present invention can be applied. Moreover, a description has been given in the above-described embodiment of a case where the dummy photodiode region includes four types of partial regions, but in the present invention, as long as a dummy photodiode region is formed along the stepped contour of the light receiving section, the effects described above can be suitably obtained even in a mode different from the above-described mode.

REFERENCE SIGNS LIST

1 . . . solid-state imaging device, 10 . . . light receiving section, 10a . . . pixel group, 11 . . . pixel, 12 . . . readout line, 13 . . . row selection line, 14 . . . semiconductor substrate, 15 . . . first conductivity-type semiconductor region, 16 . . . second conductivity-type semiconductor layer, 17 . . . oxide film, 18 . . . voltage output line, 20 . . . signal output section, 20a . . . output part, 21 . . . integration circuit, 22 . . . holding circuit, 30 . . . horizontal shift register, 30a . . . shift register part, 31 . . . shift register, 32 . . . gate, 33 . . . buffer, 40 . . . terminal electrode, 50 . . . trunk line, 61, 62 . . . buffer amplifier, 70 . . . dummy photodiode region, 70a to 70d . . . partial region, 71 . . . second conductivity-type semiconductor layer, 80 . . . passivation film, 200 . . . semiconductor wafer, $A_1$ to $A_L$ . . . row group.

The invention claimed is:

1. A solid-state imaging device comprising:
    a light receiving section having a plurality of pixels including photodiodes, respectively, the pixels being two-dimensionally arrayed in M rows and N columns;
    N readout lines disposed for the respective columns, and connected with the photodiodes included in the pixels of the respective columns via readout switches;
    a signal output section for outputting a voltage value according to an amount of charge input through each of the readout lines; and
    a vertical shift register for controlling an opening and closing operation of the readout switch for each of the rows, wherein
    a contour between one side of the light receiving section extending along a row direction and a pair of sides of the light receiving section extending along a column direction has a stepped shape,
    the solid-state imaging device further comprises a dummy photodiode region formed along the stepped contour of the light receiving section.

2. The solid-state imaging device according to claim 1, wherein
the light receiving section is configured such that L (where $L \geqq 2$) row groups each of which includes a plurality of rows having the same quantity of columns and arranged in the column direction, and
the stepped contour of the light receiving section is realized by quantities of columns $N_{L-LA+1}$ to $N_L$ of a consecutive LA (where $2 \leqq LA < L$) row groups including a row group that has a quantity of columns $N_L$, and is located at one end in the column direction out of the L row groups satisfying $N_L < N_{L-1} < \ldots < N_{L-LA+1}$.

3. The solid-state imaging device according to claim 2, wherein
the vertical shift register is disposed along an end column of each of the L row groups, and
at least a part of the dummy photodiode region is formed between respective parts of the vertical shift register corresponding to respective row groups of the light receiving section and the row groups.

4. The solid-state imaging device according to claim 2, further comprising a trunk line provided extending along the column direction of the light receiving section to supply signals and electrical power to respective parts of the vertical shift register corresponding to respective row groups of the light receiving section, wherein
at least a part of the dummy photodiode region is formed along both sides of the trunk line.

5. The solid-state imaging device according to claim 2, further comprising a trunk line provided extending along the column direction of the light receiving section to supply signals and electrical power to respective parts of the vertical shift register corresponding to respective row groups of the light receiving section, wherein
the dummy photodiode region is formed in a region except immediately under the trunk line.

6. The solid-state imaging device according to claim 4, further comprising a plurality of buffer amplifiers corresponding to the respective row groups of the light receiving section, wherein
the trunk line and the parts of the vertical shift register are connected via the buffer amplifiers, respectively.

7. The solid-state imaging device according to claim 1, wherein the dummy photodiode region has the same semiconductor layer structure as that of the photodiode.

* * * * *